US 7,033,346 B2

United States Patent
Previn et al.

(10) Patent No.: US 7,033,346 B2
(45) Date of Patent: Apr. 25, 2006

(54) OPHTHALMIC LASER SYSTEM (75) Inventors: Victor Previn, Adelaide (AU); Alexei Tikhomirov, Adelaide (AU); Dmitri Feklistov, Adelaide (AU); Malcolm Plunkett, Adelaide (AU)

(73) Assignee: Ellex Medical Pty. Ltd., Adelaide (AU)

( * ) Notice: Subject to any disclaimer, the term of this patent is extended or adjusted under 35 U.S.C. 154(b) by 0 days.

(21) Appl. No.: 10/474,761

(22) PCT Filed: Apr. 12, 2002

(86) PCT No.: PCT/AU02/00475
§ 371 (c)(1),
(2), (4) Date: Apr. 14, 2004

(87) PCT Pub. No.: WO02/083041
PCT Pub. Date: Oct. 24, 2002

(65) Prior Publication Data
US 2004/0158234 A1 Aug. 12, 2004

(30) Foreign Application Priority Data
Apr. 12, 2001 (AU) .................................... PR4421

(51) Int. Cl.
*A61B 18/18* (2006.01)
(52) U.S. Cl. .................. 606/4; 606/5; 606/10; 606/17; 600/101; 600/167; 359/368; 359/384
(58) Field of Classification Search .................. 606/4, 606/5, 10, 13, 16, 17; 600/101, 103, 109–111, 600/167, 168, 175–177; 359/368, 372, 380, 359/381, 384, 432, 433
See application file for complete search history.

(56) References Cited

U.S. PATENT DOCUMENTS

| 4,765,336 A | | 8/1988 | Blaha et al. |
| 5,000,560 A | | 3/1991 | Papritz et al. |
| 5,002,386 A | | 3/1991 | Reis |
| 5,219,347 A | * | 6/1993 | Negus et al. ................. 606/17 |
| 5,226,903 A | * | 7/1993 | Mizuno ....................... 606/17 |
| 5,342,351 A | | 8/1994 | Blaha et al. |
| 5,360,424 A | * | 11/1994 | Klopotek ...................... 606/4 |
| 5,403,307 A | * | 4/1995 | Zelman ........................ 606/6 |
| 5,425,729 A | | 6/1995 | Ishida et al. |
| 5,442,487 A | * | 8/1995 | Mizuno ...................... 359/784 |
| 5,445,146 A | | 8/1995 | Bellinger |
| 5,488,443 A | | 1/1996 | Ota et al. |
| 5,817,088 A | * | 10/1998 | Sterling ........................ 606/4 |
| 5,951,596 A | | 9/1999 | Bellinger |

(Continued)

FOREIGN PATENT DOCUMENTS
EP 0947183 A2 10/1999

*Primary Examiner*—A. Farah
(74) *Attorney, Agent, or Firm*—Cowan, Liebowitz & Latman, P.C.; Mark Montague (57) ABSTRACT

An ophthalmic laser system (1) for performing procedures such as Retinal Photocoagulation and Laser Trabeculoplasty comprises a delivery module (2) and a console module (3). The console module includes a treatment laser and optical elements for directing output from the treatment laser to an optical fiber (16), which is substantially enclosed within the delivery module. The delivery module includes a slit lamp tower (6), viewing microscope (4) and alignment optics for directing and focusing output from the optical fiber to a patient treatment zone.

13 Claims, 7 Drawing Sheets

U.S. PATENT DOCUMENTS

| | | | |
|---|---|---|---|
| 5,954,711 A | * 9/1999 | Ozaki et al. | 606/10 |
| 6,149,643 A | * 11/2000 | Herekar et al. | 606/4 |
| 6,162,210 A | * 12/2000 | Shadduck | 606/5 |
| 6,208,460 B1 | * 3/2001 | Degenhardt et al. | 359/385 |
| 6,447,504 B1 | * 9/2002 | Ben-Haim et al. | 606/15 |
| 6,663,621 B1 | * 12/2003 | Winston et al. | 606/10 |

* cited by examiner

OPHTHALMIC LASER SYSTEM

This invention relates to a treatment laser instrument designed for use by ophthalmologists for performing procedures such as, Retinal Photocoagulation, Pan Retinal Photocoagulation, Photocoagulation for Macular Degeneration and Laser Trabeculoplasty. In particular, it relates to an ophthalmic laser system having enclosed optical elements, and incorporating fiber optic beam delivery.

BACKGROUND TO THE INVENTION

The use of lasers for ophthalmic surgery is well established. There has been constant variation and improvement to the delivery systems for directing the treatment laser beam to the region of the eye that is to receive the treatment. A high degree of pointing accuracy is required because of the sensitivity of the eye and the delicate nature of the surgery. A standard approach is to use an instrument that includes a conventional slit lamp microscope for use by the surgeon to view the eye, an aiming laser, and the treatment laser which is arranged to be coincident with the aiming laser.

The treatment laser beam can be delivered according to a number of different scenarios. An early approach was to deliver the treatment laser beam via the slit-lamp illumination path. This approach is described in U.S. Pat. No. 4,765,336, assigned to Carl-Zeiss-Stiftung. Variations on the same principle can be found in U.S. Pat. No. 5,000,560, assigned to Haag-Streit, and U.S. Pat. No. 5,425,729, assigned to Kowa Company Ltd and Coherent Incorporated. The problem with this approach is that the position of the treatment laser beam moves with the position of the slit lamp illumination. This is undesirable since it limits the ability of the surgeon to adjust the treatment laser beam completely independently from the slit lamp illumination.

A second approach is to deliver the treatment laser beam via a dichroic beam splitter that is placed in front of the viewing microscope objective lens. Reference may be had to U.S. Pat. Nos. 5,226,903 and 5,954,711, both assigned to Nidek Co Ltd, for a description of this approach. Both of these patents describe the use of a fiber-optic delivery system for bringing the treatment laser beam and the aiming beam to the viewing microscope. This type of system is typically an external accessory that is attached to the top of the slitlamp microscope, normally as a retrofit. This configuration suffers from a reduction in the working distance between the slitlamp objective lens and the patient's eye due to the positioning of the beam splitter. The beam splitter also introduces astigmatic aberrations into the viewing and illumination paths, reduces the sharpness of the viewing area, restricts the laser wavelengths that can be used, adds discolouration and increases cost. In addition, because the delivery system is fitted by the user as an accessory, correct operation is dependant on the ability of the user to correctly align it. The introduction of additional optical surfaces outside of the slit lamp microscope housing also greatly increases problems with dust, scratches, breakage of optics and ghost reflections. The fiber cable is exposed and prone to potential overbending and breakage.

The wavelength restrictions and astigmatic aberrations can be minimized by delivering the treatment laser beam via a broadband mirror positioned between the viewing paths of the left and right sides of the stereo viewing microscope. Such an arrangement is described in U.S. Pat. No. 5,002,386, assigned to G Rodenstock Instruments GmbH. The arrangement fails to address the remaining shortcomings listed above.

The prior art ophthalmic laser systems each suffer from one or more disadvantages as discussed above. The use of a fiber-optic delivery system offers advantages but external positioning of the fiber subjects the laser to likely damage. A better arrangement is required.

SUMMARY OF THE INVENTION

In one form, although it need not be the only or indeed the broadest form, the invention resides in an ophthalmic laser system comprising:

a console module including a treatment laser and optical elements within said console module directing output from the treatment laser to an optical fiber;

a delivery module including a slit lamp assembly, a viewing microscope which allows viewing of a treatment zone, and alignment optics directing and focusing laser beam output from the optical fiber to the treatment zone, wherein a whole of the optical fiber is substantially enclosed within a support arm of the viewing microscope;

said alignment optics including a micromanipulator substantially enclosed within the support arm of the viewing microscope, the micromanipulator comprising a lens mounted on a pivotable arm, wherein pivoting of said lens about an optical axis by manual adjustment of a lever by a user translates to movement of a focused output of the optical fiber at the treatment zone, wherein the XY directional movement of said lever is translated to corresponding XY directional movement of the laser beam at the treatment zone; and a fixed folding mirror located within the delivery module and between the stereo viewing paths of the viewing microscope to allow simultaneous viewing of the treatment zone and laser treatment, said folding mirror directing the laser beam output from the lens of the micromanipulator to the treatment zone.

The console module suitably also includes an aiming laser, power supply, and safety and control modules.

The optical elements are preferably arranged on an optical bench within the console module. The optical bench may include means for coupling the outputs from the treatment laser and the aiming laser into the optical fiber.

The optical fiber is preferably entirely enclosed within the microscope support arm.

The folding mirror may direct output from the micromanipulator lens to the treatment zone via an objective lens of the viewing microscope.

The viewing microscope may also include a magnification changer.

A first end of the optical fiber is preferably fixed within the delivery module and a second end is suitably connectable to a connection on the console module.

Suitably there is only a single optical connection and a single electrical connection between the console module and the delivery module.

Suitably, the output of the optical fiber is passed through an optical zoom within the support arm of the viewing microscope to allow adjustment of the laser beam spot size at the treatment zone.

BRIEF DESCRIPTION OF THE DRAWINGS

To assist in understanding the invention, preferred embodiments will be described with reference to the following figures given by way of example only in which.

DETAILED DESCRIPTION OF THE INVENTION

Figure 1:
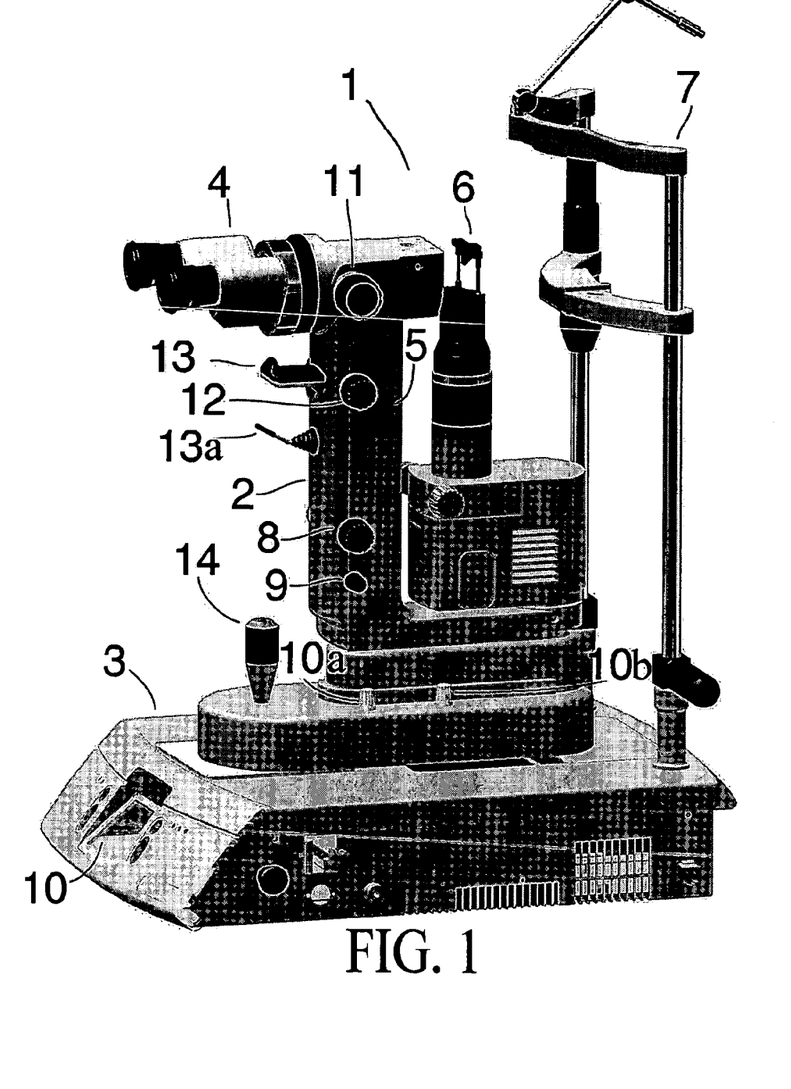
FIG. 1 shows a general view of an ophthalmic laser system.

Referring to FIG. 1, there is shown an ophthalmic laser system generally indicated as 1. The system is designed to be easily transportable by quick disassembly into a delivery module 2 and console module 3, for packing into two carry cases.

The delivery module 2 includes a stereo viewing microscope 4, mounted on a support arm 5. A conventional slit lamp tower 6 is mounted behind the support arm 5 and a patient support 7 is located behind the slit lamp tower 6. A laser indirect ophthalmoscope (LIO) (not shown) may be used instead of the delivery module 2.

The slit lamp tower 6 has the normal adjustments of slit width and rotation, illumination aperture and filter selection. Illumination intensity is controlled at the base of the slit lamp by knob 10a.

The support arm 5 encloses a magnification changer that is adjusted by knob 11, an optical zoom adjusted by knob 12 and a beam micromanipulator adjusted by lever 13. These devices are described in greater detail below with reference to FIG. 2.

The delivery module 2 is positioned with respect to the console module 3 using the XYZ joystick 14.

The output power and duration of the treatment beam are controlled with the knobs 8 and 9 respectively. The aiming beam intensity is adjusted by knob 10b.

Figure 2:
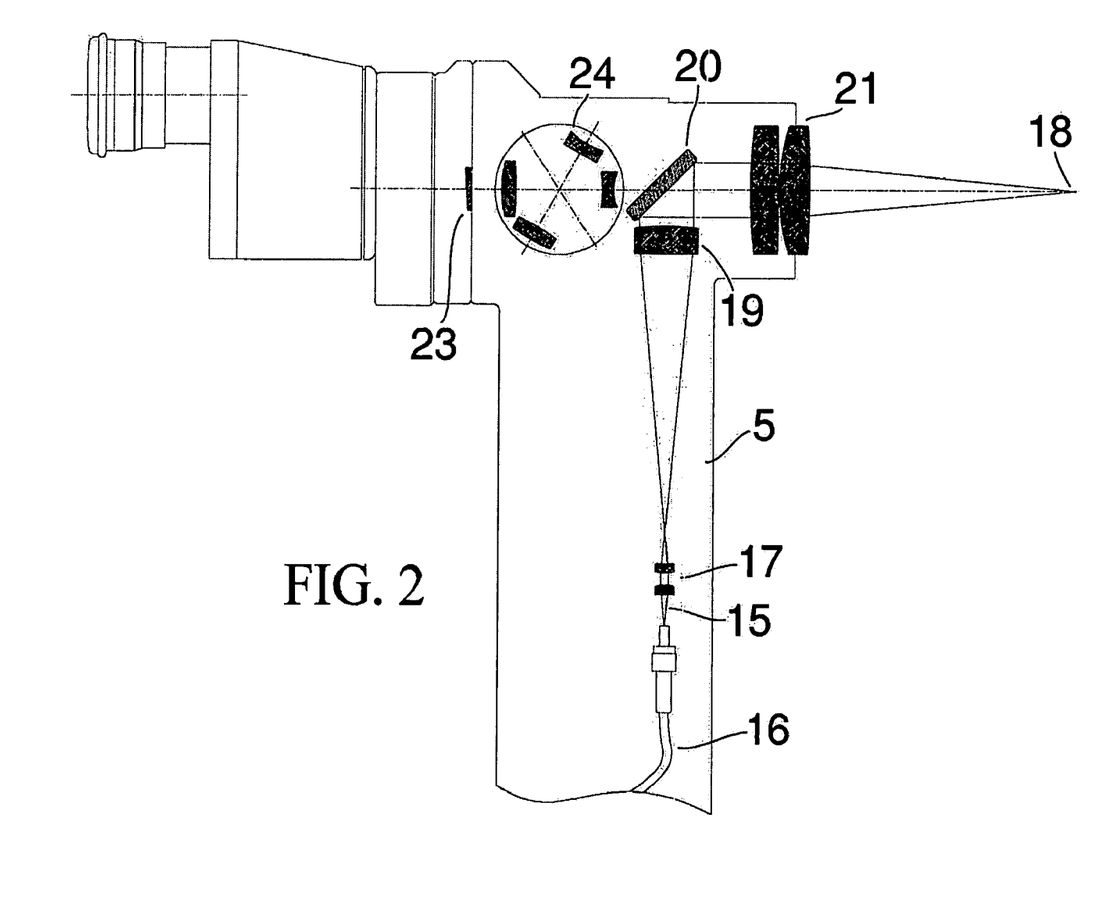
FIG. 2 shows a schematic side view of a portion of the delivery module.

The optical layout of the delivery module 2 is shown schematically in FIG. 2. Laser radiation 15 is delivered to the optical layout by a fiber cable 16. A first end of the optical fiber is fixed within the delivery module and a second end is connectable to a connection on the console module. The laser radiation includes the treatment laser beam and the aiming laser beam, which are described below.

An optical zoom 17 collects the divergent light from the fiber and adjusts the optical beam parameters to achieve a desired spotsize at a treatment zone in a patient's eye at 18. Knob 12 adjusts the optical zoom 17 by altering the relative positions of the lenses (described later herein) with respect to the end of the fiber. The fiber aperture location is adjustable for manufacturing alignment purposes.

The combined treatment and aiming beams at 18 are positioned in a small area around the center of view of the viewing microscope 4 in the focal plane by movement of a lever 13 that protrudes through a dust proof boot at the front of the support arm 5. The lever 13 rotates the position of the micromanipulator lens 19 around a swivel point before being redirected by a folding mirror 20. Lever 13 allows manipulation of the micromanipulator lens 19 about an axis transverse to the optical axis. This manipulation translates to an XY adjustment of the focused laser spot at the treatment zone within a 6 mm diameter central area of the field of view of the viewing microscope 4. A finger rest 13a is provided above the manipulator arm to reduce fatigue and assist with fine positioning.

A damper mechanism provides self-centering of the micromanipulator lens and removes hand vibrations. The damper mechanism is constructed to provide equal resistance to movement of the arm in both axes.

These devices are described in greater detail below with reference to FIG. 7 and FIG. 8.

Figure 3:
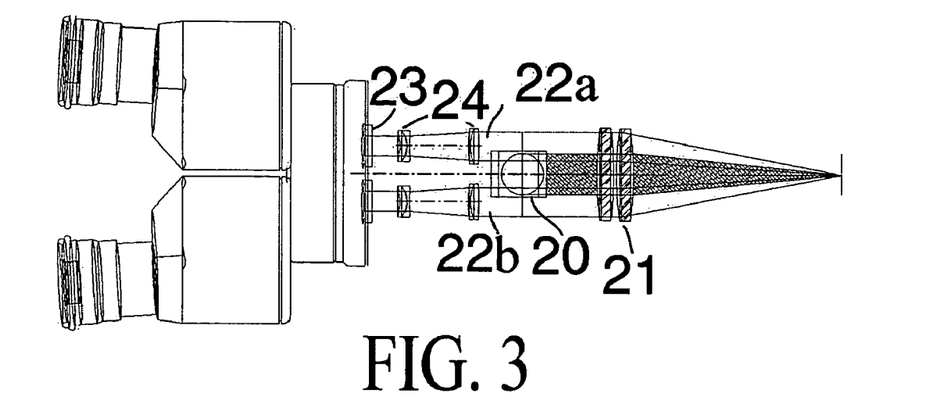
FIG. 3 shows a schematic top view of the optical layout in the delivery module.
Figure 4:
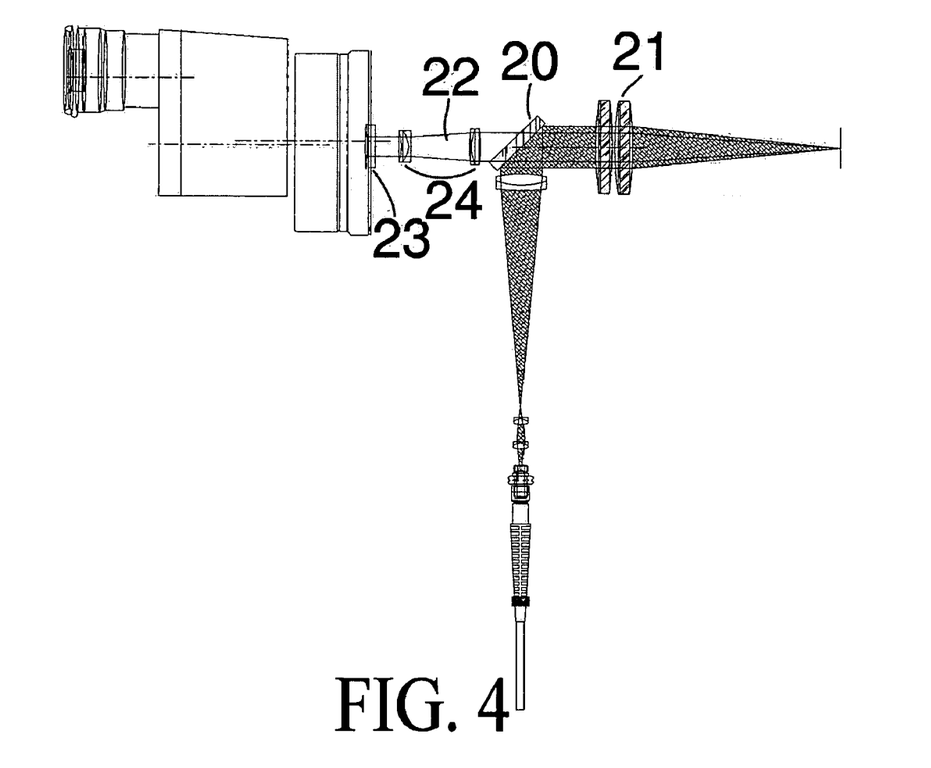
FIG. 4 shows a schematic side view of the optical layout in the delivery module.

The folding mirror 20 directs the laser beams through an objective lens 21 that provides the final focus of the aiming beam and the treatment laser beam into the patient's eye. The folding mirror assembly reflects the beams through 90 degrees so that they are coaxial with the users viewing axis and can exit the system through the objective lens 21. The folding mirror 20 is located so that it does not interfere with the field of view of the microscope by being narrow and placed midway between the viewing axes of both eyes, as seen most clearly in FIG. 3 and FIG. 4. The folding mirror 20 is positioned between the stereo viewing paths 22a,b of the viewing microscope 4.

As seen in FIG. 2, a safety filter 23 is placed in the viewing path of the viewing microscope. The magnification of the viewing microscope can be changed by rotating the magnification changer 24.

Figure 5:
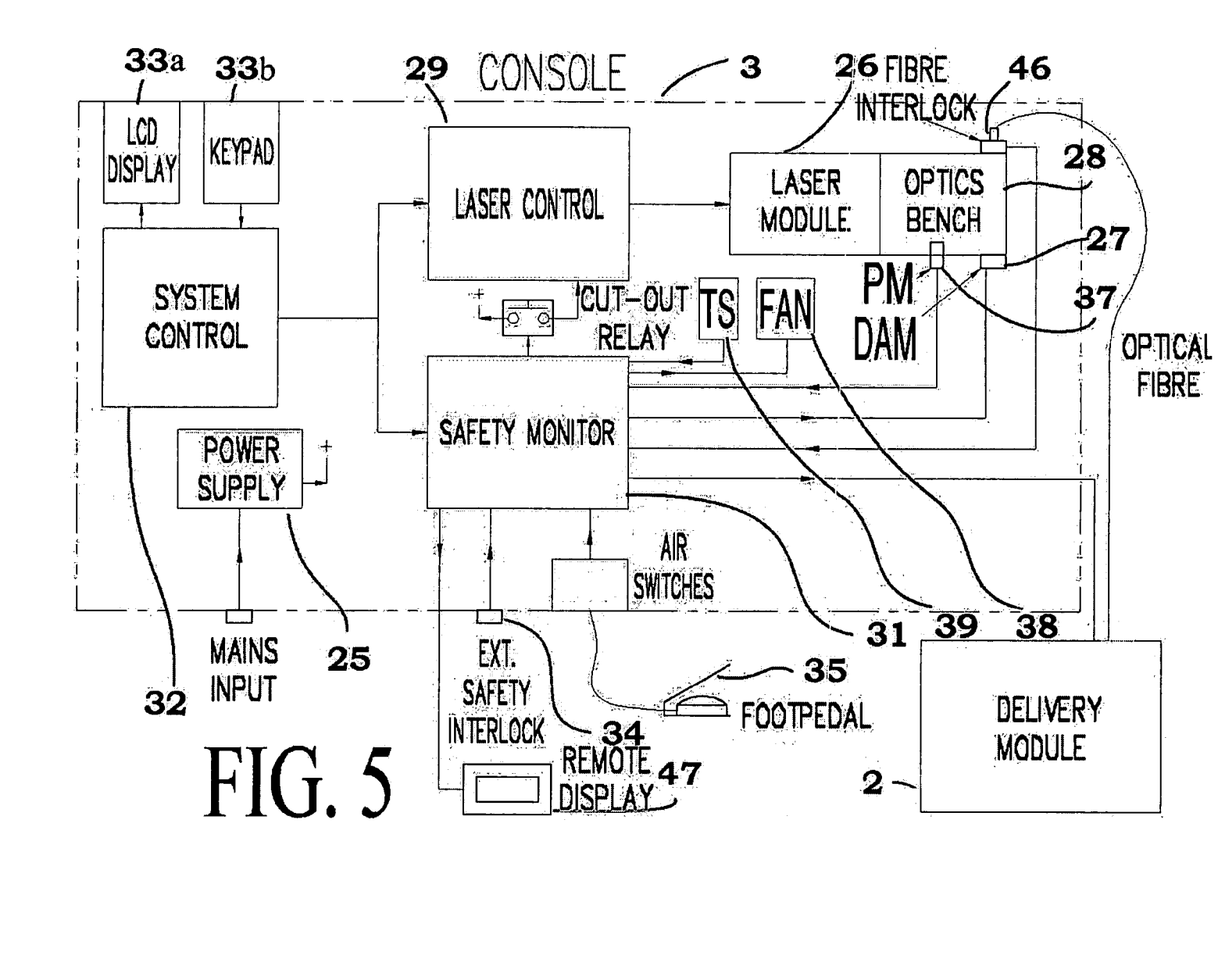
FIG. 5 shows a block diagram of the console module.

A functional block diagram of the console module 3 is shown in FIG. 5. The console module 3 contains a switch mode power supply 25 that provides all power required for operation of the laser system, including the treatment laser module 26 and aiming laser 27 on optical bench 28, laser control module 29, safety monitor module 31 and system control module 32.

The switched mode power supply module 25, laser control module 29, treatment laser module 26, optical bench 28, safety monitor module 31 and system control module 32 are all replaceable elements that can be easily disconnected and removed without disruption to the remaining elements.

The treatment laser module 26 is a diode pumped solid state laser at 532 nm producing in excess of 1 Watt average power of light in the treatment beam. The power level of the treatment beam is adjustable in steps between 30 mW and maximum power. The spot size of the treatment beam can be continuously varied between 50 μm and 1000 μm. The ophthalmic laser system delivers treatment laser power in pulses with selectable pulse durations ranging from 10 ms to 4 s. In an auto-repeat mode the interval between pulses can be selected from 100 ms to 1 s.

The aiming laser 27 is a red semiconductor laser operating at a wavelength of 635 nm. The treatment laser module and the aiming laser are combined on an optical bench 28.

The system control module 32 contains a microprocessor PCB connected to a display 33a and six user control buttons on a keypad 33b. The microprocessor monitors and controls functions associated with the laser system by communicating serially with the laser control module 29 and the safety monitor module 31. It also contains an audible indicator to warn of laser emission and interlock operation, a visible indicator of laser emission and visible indicators for ready and standby status.

The safety monitor module 31 has connections to and from the power supply 25, the delivery module 2, system control module 32, laser control module 29, external safety interlock 34, footswitch 35, aiming laser 27, power monitor 37, fan 38 and ambient temperature sensor 39. A remote display 47 is provided for remote monitoring of the main treatment parameters. The remote display port can also be viewed for diagnostic functions.

Figure 6:
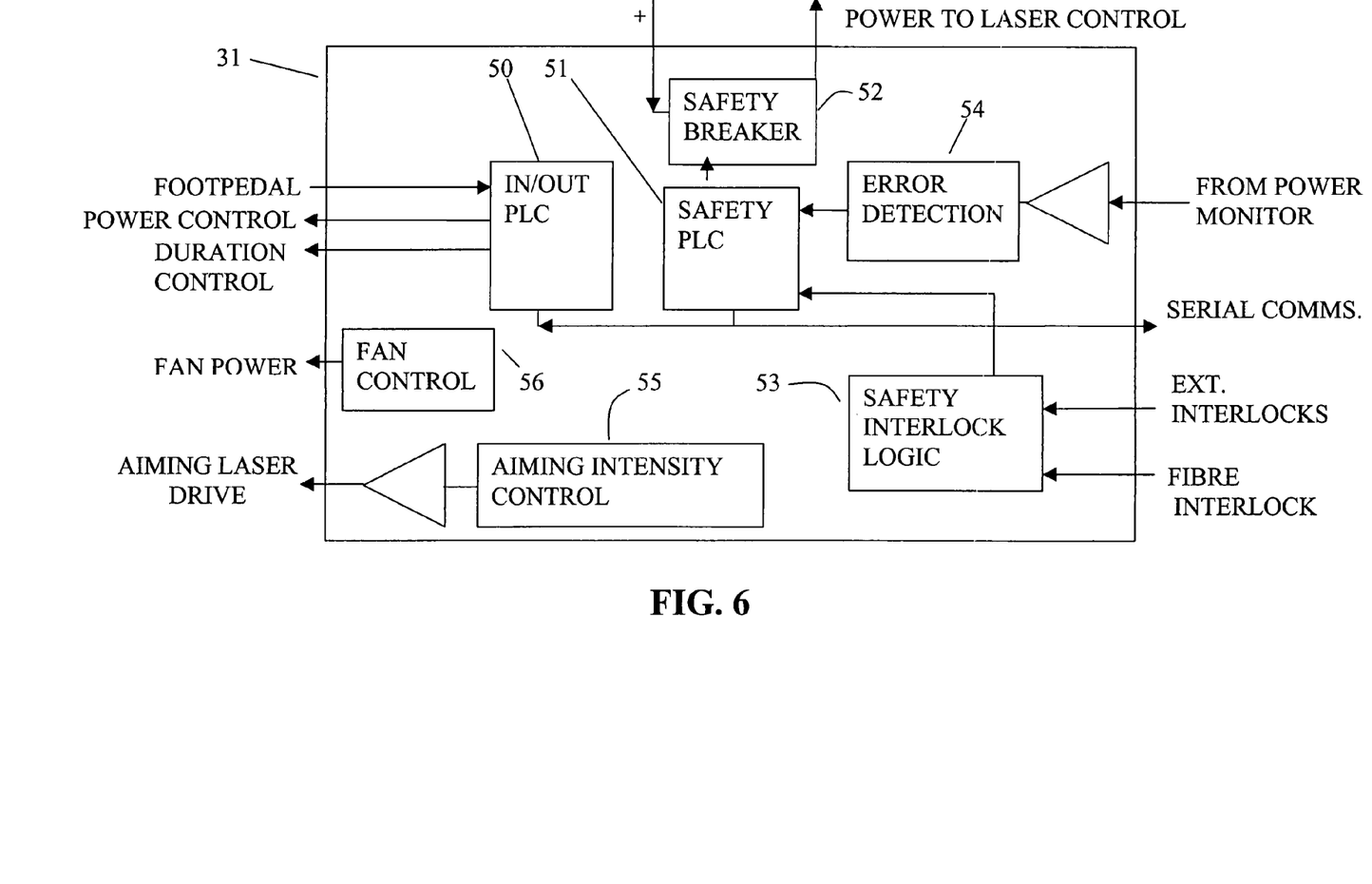
FIG. 6 shows a block diagram of the safety monitor module.

A functional block diagram of the safety monitor module 31 is shown in FIG. 6. The safety monitor module 31 has central control of the operation of the laser system. A first programmable logic controller (PLC) 50 processes all signals and controls for interface to the system control module 32. A second PLC 51 provides a redundant safety monitor circuit. The second PLC of the safety monitor module 31 monitors all treatment beam firings independent of the system control module 32, and is responsible for shutting down the laser control module 29 when a hazardous condition is identified.

With further reference to FIG. 6, any one or combination of a safety breaker circuit 52, safety interlock logic unit 53 or error detection unit 54 of the safety monitor module 31 may identify such hazardous conditions. The safety breaker circuit 52 prevents power being supplied to the laser control module 29 in excess of a preset power level which may be set by the user using the keypad 33*b*. The safety interlock logic unit 53 compares the outputs of the interlocks with the desired settings and communicates any anomalies to the second PLC 51. Error detection unit 54 receives input from the power monitor 37 and communicates any errors in the power level to the second PLC 51. Safety monitor module 31 also comprises an aiming laser intensity control unit 55 and a fan control unit 56.

The laser control module 29 controls the treatment laser module 26 and communicates with the system control module 32 to allow this to set the parameters of the treatment laser beam and turn it on and off. It interfaces to the electrical elements of the delivery head and contains the display and control elements of the user interface mounted on the control panel 10.

Figure 7:
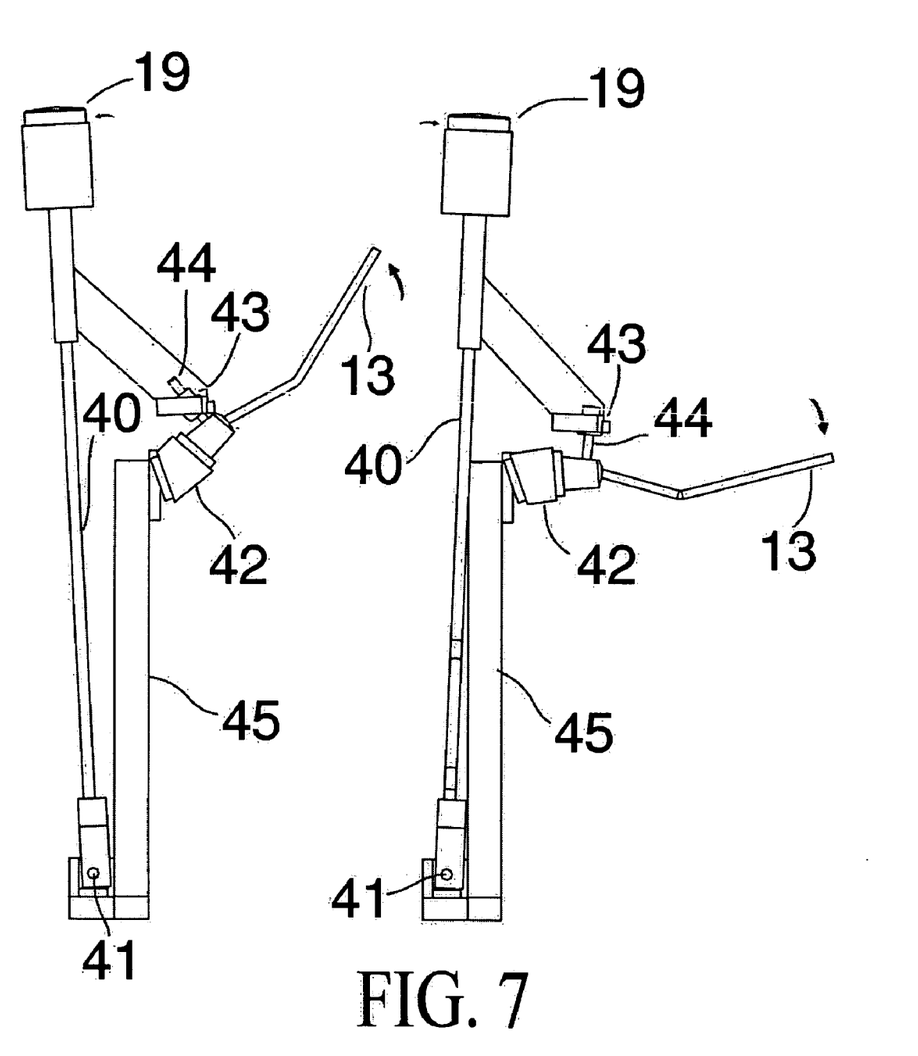
FIG. 7 shows a schematic side view of the micromanipulator mechanism.
Figure 8:
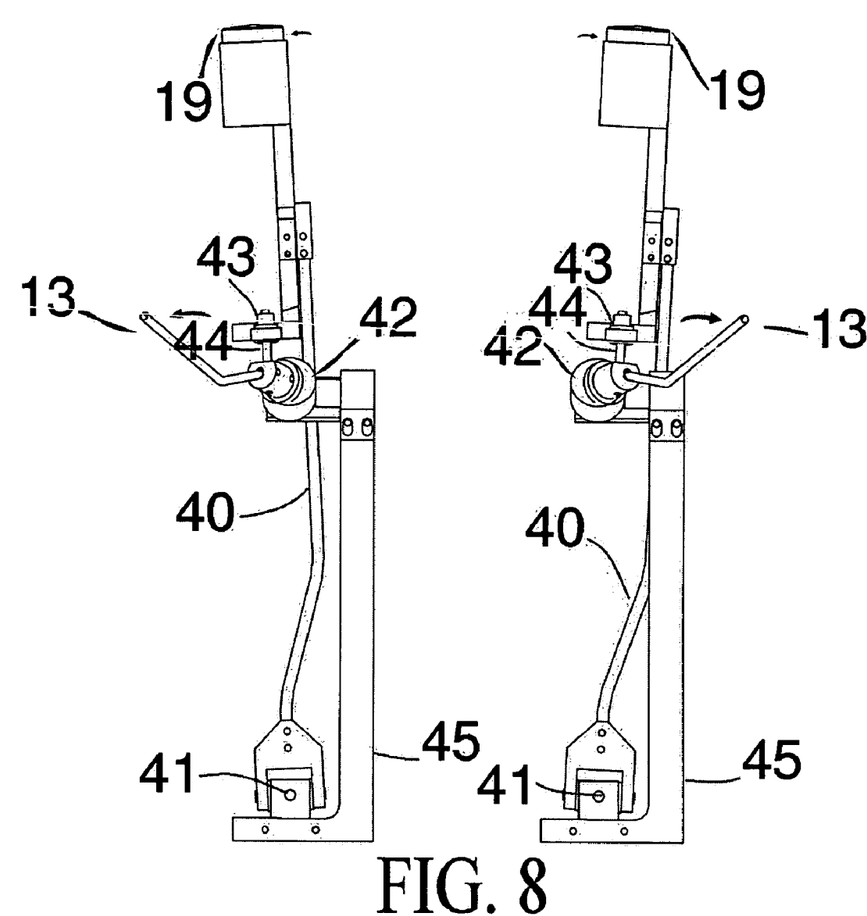
FIG. 8 shows a schematic front view of the micromanipulator mechanism.

FIG. 7 and FIG. 8 show the working principle of the micromanipulator referred to above. Lever 13 bends the damper mechanism 42 acting as a torsion bar to transfer the movement to the pivoting arm 40 through the sliding shaft 44 and a spherical bearing 43. The pivoting arm 40 holds the micromanipulator lens 19 and moves it around the pivot point 41 in XY directions transversally to the optical axis of the delivery module 2. The transversal displacement of the micromanipulator lens 19 translates to the XY tilt of output beam of the delivery module causing the focused laser spot at the treatment zone 18 to move within a 6 mm diameter area. The damper mechanism 42 is constructed to provide equal resistance to movement of the lever 13 in both axes. The damper mechanism also provides self-centering for the micromanipulator lens 19 and removes hand vibrations. The assembly is supported on bracket 45 within the support arm 5.

As is evident from the foregoing description, especially with reference to FIG. 2, the optical fiber cable 16 and the alignment optics are contained wholly within the support arm 5. This overcomes the prior art problem of damage to the optical fiber. Furthermore, the delivery module 2 and the console module 3 can be separated by disconnecting an optical connection and an electrical connection. The micromanipulator allows precise adjustment of the treatment laser spot position independent of the slit lamp or viewing microscope position.

The configuration described above maintains the maximum working distance between the objective lens and the patient's eye because no external beamsplitter is required. This also eliminates the problems with astigmatic aberrations, laser wavelength restrictions, and discoloration. Potential alignment problems and damage are also avoided because the laser delivery system, including the optical fiber, is fully enclosed in the support arm of the microscope. The advantages for the ophthalmic surgeon are a clearer view of the treatment area, maximum room for positioning a surgical contact lens on the patient's eye and a more compact, robust and reliable instrument.

Furthermore, the ophthalmic laser system is easily disassembled into two modules for package into two cases. Reassembly is a simple and quick procedure. The ophthalmic laser system is accurate, portable and easy to use.

Throughout the specification the aim has been to describe the invention without limiting the invention to any one embodiment or specific collection of features. Persons skilled in the relevant art may realize variations from the specific embodiments that will nonetheless fall within the scope of the invention.

What is claimed is:

1. An ophthalmic laser system comprising:
   a console module including a treatment laser and optical elements within said console module directing output from the treatment laser to an optical fiber;
   a delivery module including a slit lamp assembly, a viewing microscope for viewing of a treatment zone, and alignment optics directing and focusing laser beam output from the optical fiber to the treatment zone, wherein a whole of the optical fiber is substantially enclosed within a support arm of the viewing microscope;
   said alignment optics including a micromanipulator substantially enclosed within the support arm of the viewing microscope, the micromanipulator comprising a lens mounted on a pivotable arm, wherein pivoting of said lens about an optical axis by manual adjustment of a lever by a user translates to movement of a focused output of the optical fiber at the treatment zone, wherein XY directional movement of said lever is translated to corresponding XY directional movement of the laser beam at the treatment zone; and
   a fixed folding minor located within the delivery module and between stereo viewing paths of the viewing microscope to allow simultaneous viewing of the treatment zone and laser treatment, said folding mirror directing the laser beam output from the micromanipulator lens to the treatment zone.

2. The ophthalmic laser system of claim 1, wherein the console module further includes an aiming laser.

3. The ophthalmic laser system of claim 1, wherein the console module further includes a power supply.

4. The ophthalmic laser system of claim 1, wherein the console module further includes a safety monitor module.

5. The ophthalmic laser system of claim 1, wherein the console module further includes a control module.

6. The ophthalmic laser system of claim 1, wherein the optical elements are arranged on an optical bench within the console module.

7. The ophthalmic laser system of claim 6, wherein the optical bench includes means for coupling the outputs from the treatment laser and an aiming laser into the optical fiber.

8. The ophthalmic laser system of claim 1, wherein the optical fiber is entirely enclosed within the microscope support arm.

9. The ophthalmic laser system of claim 1, wherein the folding mirror directs output from the lens of the micromanipulator to the treatment zone via an objective lens of the viewing microscope.

10. The ophthalmic laser system of claim 1, wherein the viewing microscope includes a magnification changer.

11. The ophthalmic laser system of claim 1, wherein a first end of the optical fiber is fixed within the delivery module and a second end is connectable to a connection on the console module.

12. The ophthalmic laser system of claim 1, wherein there is only a single optical connection and a single electrical connection between the console module and the delivery module.

13. The ophthalmic laser system of claim 1, wherein the output of the optical fiber is passed through an optical zoom within the support arm of the viewing microscope to allow adjustment of the laser beam spot size at the treatment zone.

* * * * *